US007566743B2

(12) United States Patent
Glazman

(10) Patent No.: US 7,566,743 B2
(45) Date of Patent: Jul. 28, 2009

(54) SYSTEM AND METHOD FOR MEDICAL TREATMENT

(76) Inventor: Mark Glazman, 2725 Floribunda Dr., Columbus, OH (US) 43209

( * ) Notice: Subject to any disclaimer, the term of this patent is extended or adjusted under 35 U.S.C. 154(b) by 358 days.

(21) Appl. No.: 11/282,251

(22) Filed: Nov. 18, 2005

(65) Prior Publication Data

US 2007/0113842 A1 May 24, 2007

(51) Int. Cl.
*A61L 9/00* (2006.01)
*A61L 9/18* (2006.01)
*A61L 9/19* (2006.01)

(52) U.S. Cl. .................. 514/826; 514/972; 250/432 R; 250/436; 422/24

(58) Field of Classification Search ................. 514/826, 514/972; 250/432 R, 436; 422/24
See application file for complete search history.

(56) References Cited

U.S. PATENT DOCUMENTS

| | | | | |
|---|---|---|---|---|
| 4,210,429 | A | 7/1980 | Golstein | |
| 4,806,768 | A * | 2/1989 | Keutenedjian | 250/436 |
| 5,074,894 | A | 12/1991 | Nelson | |
| 5,330,722 | A * | 7/1994 | Pick et al. | 96/55 |
| 5,635,133 | A | 6/1997 | Glazman | |
| 5,642,728 | A * | 7/1997 | Andersson et al. | 128/203.15 |
| 5,733,939 | A | 3/1998 | Fuhrman et al. | |
| 5,997,619 | A | 12/1999 | Knuth et al. | |
| 6,264,888 | B1 | 7/2001 | Palestro et al. | |
| 6,328,937 | B1 | 12/2001 | Glazman | |
| 6,464,760 | B1 | 10/2002 | Sham et al. | |
| 6,482,391 | B1 | 11/2002 | Hills et al. | |
| 6,700,128 | B2 * | 3/2004 | Matschke | 250/432 R |
| 6,899,099 | B2 | 5/2005 | Andersson et al. | |

OTHER PUBLICATIONS

U.S. Appl. No. 11/746,360, filed May 2007, Glazman.*
U.S. Appl. No. 11/782,887, filed Jul. 2007, Glazman.*

* cited by examiner

*Primary Examiner*—Mina Haghighatian
(74) *Attorney, Agent, or Firm*—David L. King

(57) ABSTRACT

This invention relates to a system for and method for medical treatment of respiratory diseases. The system and method are particularly effective for the treatment of and protection from diseases associated with allergic inflammation. Suitable diseases for treatment include atopic asthma, rhinitis, sinusitis, and conjunctivitis.

17 Claims, 1 Drawing Sheet

SYSTEM AND METHOD FOR MEDICAL TREATMENT

The United Stated Government has certain rights in this invention by virtue of National Institute of Health Grant No. 1 R43 AI053967-01.

FIELD OF THE INVENTION

This invention concerns a system and a method for treatment of respiratory diseases.

BACKGROUND OF THE INVENTION

Approximately twenty million individuals or 5% of the United States population suffer from asthma and 20% suffer from allergic rhinitis. Successful clinical management of asthma in children has the potential to decrease this burden by lowering the disproportionate costs of hospitalization and acute care for pediatric asthma patients. Despite increased knowledge regarding the pathogenesis of the disease and the availability of effective anti-inflammatory agents, particularly inhaled corticosteroids, the prevalence of asthma and disease-related morbidity continues to remain high in children.

It is widely believed that a major contributing factor to the rising prevalence of these disorders is poor indoor air quality and the allergens contained in that air. Indoor environments are sources of many common allergens such as dust mites, mold spores, cockroaches, pets and their by-products, which have been linked with adverse health effects. This has led to the belief that effective treatment should include filtering out the allergens and administration of drugs which reduce the sensitivity of asthma sufferers to allergens.

There are known air purification systems which filter and irradiate air by germicidal ultraviolet to prevent spread tuberculosis and other infectious diseases (U.S. Pat. Nos. 6,264,888; 6,464,760; 5,997,619; 4,210,429). These and other known air purification system are able substantially purify the air but did not affect the health of asthmatic patients. The studies of health effect of air filtration did not demonstrate significant improvement in any measure of the disease activity (R. Wood at al., A Placebo-controlled Trial of a HEPA Air Cleaner in the Treatment of Cat Allergy, AM J RESPIR CRIT CARE MED 1998;158: 115-120.; E. McDonald at al. Effect of Air Filtration Systems on Asthma, Chest. 2002;122: 1535-1542)

There are number of ultraviolet germicidal systems that have been patented, but as in the case of the scientific literature mentioned above, those patents teach little about how to position and operate the devices to achieve health effect in asthmatic and allergic patients.

For example, U.S. Pat. No. 4,210,429 by Golstein, employs a "squirrel-cage" type blower which draws air into an enclosure through an air intake filter, through the blower, and through a sterilization chamber containing ultraviolet lights. The air leaves the sterilization chamber, passes through a second filter and a charcoal filter and finally exits through an outlet. The specification indicates that the purpose of the device is to remove "pollens, lung damaging dust, smoke, bacteria and any one of a number of other irritants and microorganisms" and that it does so for "particles down to 0.3 microns in size with an efficiency of 99.9%". The device has three distinct filters including a very fine filter for removing extremely small particles, a charcoal filter for removing odors and a pre-filter for removing particles. This extensive filtration would require a powerful blower to achieve effective air purification. The device designed for air purification. Therefore, the patent teaches nothing about the use of the device for the purpose for treatment of respiratory diseases or the optimal irradiation of the air flow or the positioning of the device for that purpose.

U.S. Pat. No. 5,074,894 by Nelson is for a hospital room to quarantine patients with tuberculosis or other respiratory diseases caused by airborne pathogens. Although one embodiment of the system includes an air circulation circuit with ultraviolet lights, the patent teaches nothing about the use of the device for the purpose for treatment of respiratory diseases.

U.S. Pat. No. 6,264,888 by Palestro teaches about an apparatus and process for destroying airborne pathogenic bacteria such as the tuberculosis bacteria. Ultraviolet lights of a sufficient intensity are positioned within a sterilization chamber where they kill bacteria suspended in the form of microdroplets of sputum in the air stream. The apparatus is configured to fit behind a wall in a room, or preferably, above a suspended ceiling. The patent teaches nothing about the use of the device for the purpose for treatment of respiratory diseases or the optimal irradiation of the air flow or the positioning of the device for that purpose.

U.S. Pat. Nos. 5,635,133 and 6,328,937 by Glazman teach about a method and apparatuses for killing microorganism in a flowing fluid medium using germicidal beams as a means for killing the microorganisms in a straight portion of the flow path. These patens teach about effective, economical, and reliable method and apparatus for air or liquids disinfection. The patents teach nothing about the use of the apparatuses for the purpose for treatment of respiratory diseases or the optimal irradiation of the air flow or the positioning of the device for that purpose.

It is recognized among almost all physicians that systemic corticosteroids are usually required for the treatment of severe asthmatics. Systemic corticosteroids have significant anti inflammatory effects and, if given early enough to an asthmatic, they can effectively shorten the length and decrease the severity of acute asthma. However, when given over the long term for severe chronic asthma, such efficacy, for this condition, is accompanied by a long list of severe side effects, including cataracts, hypertension, diabetes, peptic ulcer, osteoporosis, poor wound healing, adrenal suppression, etc. Many frequently prescribed drugs are suspected to cause acute or drug-induced pancreatitis (Trivedi CD, J Clin Gastroenterol. 2005 September;39(8):709-16). The risk of developing of side effects and complications could be reduced by lowering the consumption of the drugs; however, this is not advisable because it would reduce the effectiveness of the treatment.

There is known a method for reducing the inflammatory response in tissues of a patient, by contacting the tissue with an effective, inflammation-reducing amount of a liquid or gaseous fluorocarbon (U.S. Pat. No. 5,733,939). This method requires complicated technique of fluorocarbon delivery and safety concerns because fluorocarbon propellants may be hazardous if they are deliberately abused. Inhalation of high concentrations of aerosols sprays has brought about cardiovascular toxic effects and even death, especially under conditions of hypoxia.

There are also known (U.S. Pat. No. 6,482,391) method of treatment of asthma comprising a surface active phospholipid (SAPL) is prepared in the form of a fine powder and administered to the lungs in a gas stream. The application of this treatment or the application of the steroids involves the risk of side effects and adverse events, such as liver damage or viral/fungal infections.

Although we do not wish to be bound by any particular theory of the invention, the present invention is based on the approach that the airway inflammation and reactivity associated with asthma could be reduced by lowering the level of exposure to extrinsic factors associated with asthma and by exposing the patient to denatured airborne allergens.

SUMMARY OF THE INVENTION

It is an object of the present invention to provide an efficacious system and method for the treatment of respiratory diseases with the benefit of reducing the severity of the disease in a manner proven to be safe for children.

It is a further object of the present invention to provide an adjuvant treatment for use with medication for the treatment of respiratory diseases whereby reduction of dosage, without contra indications, is possible, resulting in the reduced severity of the side effects of the said medications.

It is a still further object of the present invention to provide an efficacious medication treatment for asthmatic conditions with a technique having a long standing documented history of safe use (over 60 years) but for conditions other than for treatment of asthmatics.

It is an object of the present invention to provide a medical system for treating a disease associated with allergic airway reactivity, using treated air for breathing, the system comprising: an enclosed facility with circulating treated air for breathing, accommodating the patient susceptible to allergic airway reactivity for an effective amount of time, treated air for breathing containing particles and microorganisms, wherein treated air for breathing being comprised of substantially irradiated by ultraviolet radiation air, a chamber for the irradiation of said treated air, the chamber having an inlet end and an outlet end, reflective inner surfaces and ultraviolet lamps, located between an inlet and outlet ends; inlet and an outlet ends connected with enclosed facility by light absorbing passageway, which prevents the escape of UV radiation to outside of the passageway.

It is a further object of the invention to provide the medical system where ultraviolet lamps being located closer to inlet end of the chamber for irradiation.

It is a further object of the invention to provide the medical system where ultraviolet lamps have parabolic reflectors with the directrix pointed towards outlet end of the chamber for irradiation.

It is a further object of the invention to provide the medical system where enclosed facility being comprised of an enclosed area with controlled ventilation.

It is a further object of invention to provide the medical system where treated air circulates through the facility by 1-15 air changes per hour.

It is a further object of the invention to provide a method of treating a disease associated with allergic airway reactivity, using treated air for breathing, the method comprising of steps of: providing an enclosed facility with circulating treated air for breathing; accommodating the patient susceptible to allergic airway reactivity for an effective amount of time; providing a chamber for the irradiation of the air for breathing, the chamber having an inlet end and an outlet end, reflective inner surfaces and ultraviolet lamps, located between an inlet and outlet ends closer to the inlet end, wherein an effective amount of incident UV radiation applies to the air for breathing; providing light absorbing passageway, connecting inlet and outlet ends with an enclosed facility, preventing the escape of UV radiation to the outside of the passageway, and providing air containing particles and microorganisms.

It is a further object of the invention to provide the emission of ultraviolet radiation towards an outlet end of the chamber for the irradiation of treated air.

It is a further object of the invention to provide an effective amount of time for accommodating the patient susceptible to allergic airway reactivity. It was found that effective amount of time is preferably from about 6 to about 24 hours daily.

It is a further object of the invention to irradiate treated air by a parallel array of beams. The ultraviolet energy will be applied evenly and efficiently to the airflow.

It is a further object of the invention where ultraviolet radiation being comprised of radiation with the wave length of 180-400 nm.

It is a further object of the invention wherein an amount of incident UV radiation which is being applied to treated air for breathing is 2-100 J/m.sup.3 hr.

With regard to the irradiation of the air for breathing, it can be readily appreciated that CREON2000® air disinfection system may be used as a source of ultraviolet radiation and can provide steady flux of the radiation. The system can apply the radiation evenly to the air flow. The housing of the system protects the bulb from mechanical impact and turbulent air flow. An internal HEPA filter protects the bulb from dust and dirt accumulation that can dramatically reduce UVC output.

The system preferably provides UV radiation with the wavelength 185-400 nanometers. A particularly suitable system is the system with a low pressure mercury bulb with prevailing emission at 240-260 nanometers.

It has been found that the severity of asthma and the number of days with asthma symptoms can be reduced by providing incident UV radiation, which is being applied to the air for breathing. An effective amount of incident UV radiation which is being applied to the treated air for breathing is generally from about 2 to about 100 Joules per cubic meter per hour, preferably from about 8 to about 80 J/m.sup.3 hr, most preferably from about 16 to about 55 J/m.sup.3 hr.

It is a further object of the invention to provide the method of treating a disease associated with allergic airway reactivity, using treated air for breathing, the method further comprising of steps of: providing a patient with a baseline medication usage history; in subjecting the patient to treated air for breathing for an effective amount of time; and achieving a reduction from the baseline medication usage.

It is a further object of the invention to provide the method of treating a disease associated with allergic airway reactivity, using treated air for breathing wherein the patient is taking one or more of the following medications: Inhaled corticosteroids; Cromolyn; Nedocromil; Anti-leukotrienes; Theophylline; Inhaled Long-acting beta.sub.2 agonist; Inhaled Short-acting beta.sub.2 agonist; Anticholinergic; Oral Steroids.

The advantage of the present invention is the provision of accommodating the patient susceptible to allergic airway reactivity for effective amount of time in an enclosed facility with circulating treated air for breathing, the treated air for breathing being sufficiently irradiated with UV radiation. Prolong inhalation of the specifically treated air causing the reduction of allergic airway reactivity and improvement of health. This advantage makes the method and system according to the present invention an effective means for the treatment of breathing disorders and reduction of risks of the side effects. These and other features and advantages of the present invention will become more evident from the following discussion.

Definitions

FEV1. This is the volume of air expired in the first second during maximal expiratory effort. The $FEV_1$ is reduced in both obstructive and restrictive lung disease.

Peak expiratory flow rate (PEFR) is the fastest rate at which air moves through the airways during a forced expiration starting with fully inhalation. The PEFR correlates well with $FEV_1$. Peak expiratory flow rate variability (PEFRvar) is a measure of the diurnal variation in respiratory function.

Denature means modify (as a native protein) esp. by heat, acid, alkali, or ultraviolet radiation so that all of the original properties are removed or diminished.

BRIEF DESCRIPTION OF THE DRAWINGS

The invention will be described by way of example and with reference to the accompanying drawings in which.

DETAILED DESCRIPTION OF THE INVENTION

Figure 1:
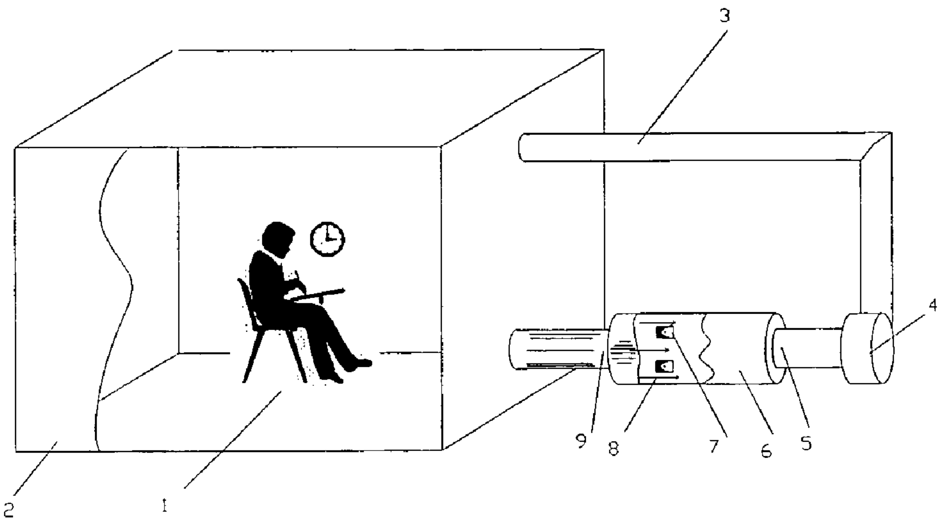
FIG. 1 is a schematic view of the system for medical treatment of respiratory diseases according to the first embodiment of the invention

FIG. 1 is a schematic view of the system for medical treatment of respiratory diseases according to the first embodiment of the invention. The patient 1 being treated in enclosed facility 2. Enclosed facility 2 connected with a chamber for the irradiation 6, which is having an inlet duct 9 and an outlet duct 10. The chamber for irradiation 6 has reflective inner surfaces and ultraviolet lamps 7, located between an inlet and outlet ends. The fan 4 connected with outlet duct 5 and with the passageway 3. The air for breathing 8 is filling up the enclosed facility 2. The patient 1 being in the enclosed facility 2 is inhaling the air for breathing 8. The fan 4 provides continuous supply of treated air for breathing for the patient 1 to inhale. The air for breathing 8 is taken out from the enclosed facility 2 by the fan 4. The air for breathing 8 is entering into chamber for irradiation 6 through inlet duct 9. In the chamber for irradiation 6 the air for breathing 8 is being irradiated by ultraviolet radiation from the ultraviolet lamps 7. The allergens and microorganisms in the air are being denatured after being irradiated in the chamber for irradiation 6. The treated air for breathing 8 is being pumped into the enclosed facility 2 by the fan 4. The patient 1 situated in enclosed facility 2 is receiving the treatment by inhaling the treated air for breathing 8 during 6-24 hours a day. The enclosed facility 2 may represent one room or a variety rooms with a common mechanical ventilation system.

Figure 2:
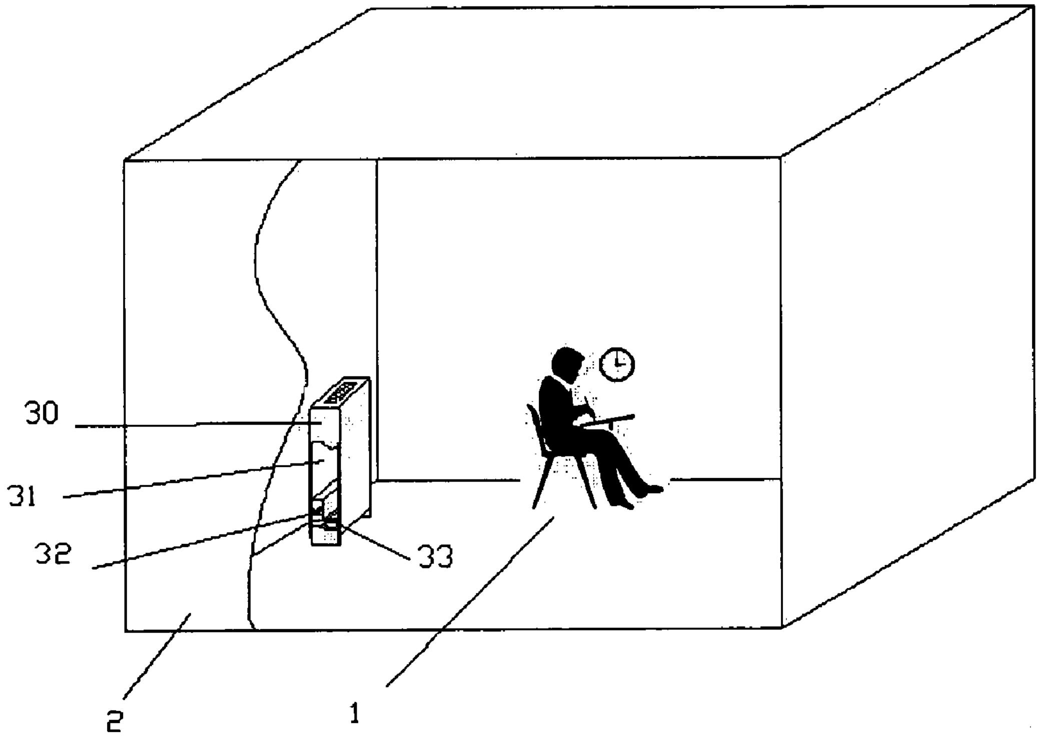
FIG. 2 is a schematic view of second embodiment of invention.

FIG. 2 is a view of second embodiment of invention. The second embodiment of the invention being when the room unit 30 containing a chamber for irradiation 31, ultraviolet lamp 32 and fan 33 is used for treating the air for breathing with sufficient amount of ultraviolet radiation. The patient being in the room 1 and inhaling treated air for breathing during 6-24 hours a day receives sufficient treatment, which improves health, reduces risk and severity of asthma.

Although the invention discusses treatment of asthma it is also intended that the invention include treatment other respiratory diseases associated with allergic inflammation, or infectious diseases.

TEST EXAMPLE 1

A Study of Effect of the CREON2000® Air Disinfection System and Placebo in Asthmatic Children.

Objectives.

The objectives of the study were to compare the efficacy and safety of a treatment of pediatric asthmatic patients by providing for breathing the air substantially irradiated by ultraviolet radiation, by using the CREON2000® Air Disinfection System as described in U.S. Pat. No. 5,635,133 in accordance with the first embodiment of the invention shown in FIG. 1.

Methodology.

This was a randomized double-blind, placebo-controlled, parallel-group study.

Number of Subjects.

The total number of patients in the study was 20, the number analyzed for efficacy was 19 and the number analyzed for safety was 19.

Diagnoses and Main Criteria for Inclusion.

Mold-sensitized asthmatic children with mild to moderate/severe asthma (FEV1>50%) between the ages 5-17 were recruited to participate in this trial. To participate, children had to be capable of performing peak expiratory flow rate (PEFR) measurements and recording asthma and rhinoconjunctivitis symptoms in a daily diary. All children had to be sensitized to at least one indoor mold allergen (*Aspergillus* and *Penicillium*) and one other indoor perennial allergen (dust mite, cockroach). They had to agree to reside in the same home during the study, they had to have a home with a central duct ventilation system and the children had to manifest asthma symptom scores>1 based on an a four point asthma severity scale. Children were excluded if they had passive or active indoor smoke exposure, pre-existing extensive remediation in the home (i.e., HEPA filters . . . ), active fireplaces and other sources of air particulates (wood burning stoves, kerosene heaters . . . ), active "in duct" humidifiers, sensitization to pets present in the home or other chronic illnesses (cystic fibrosis, etc. . . . ).

The Treatment

After the initiation of the study, participating children spent 6-24 hours per day inside of houses which were supplied with specifically treated air for breathing. The air for breathing was treated by ultraviolet radiation with the wavelength of 180-400 nm emitted by Air Disinfection System CREON2000®. For this purpose the CREON2000® Air Disinfection Systems emitting ultraviolet radiation were installed into mechanical ventilation systems in the homes of 11 children. The CREON2000® systems applied regularly the amount of 2-80 $J/m^3$ hr of incident UV radiation to the air for breathing circulating inside of the house. The Placebo system emitting blue light and not emitting ultraviolet radiation were installed into the ventilation systems of the homes of 8 children. All these houses had mechanical ventilation system comprising of passageway and a fan.

Efficacy Variables

The primary Efficacy Variables were improvement in PEFR (Peak Expiratory Flow Rate) variability and FEV1 (Flow Expiratory Volume in 1 second). Secondary endpoints were changes in total and individual asthma and rhinoconjunctivitis and symptom severity scores, changes in the number of days with the symptoms over 2 months treatment phase.

The symptom scores are based on the subjective evaluation by the patients or their parents based on a 0-4 rating system in which 0=no symptoms, 1=mild symptoms, 2=moderate symptoms, 3=severe and 4=unbearable symptoms.

Safety Variables

Safety variable were: reported adverse effects that could be due to the intervention Statistical Methods Non-parametric and parametric statistical methods were applied. ANOVA, regression analysis, and the unpaired and paired t-tests methods were used to analyze continuous data. For the ordinal data, Wilcoxon Paired Signed Rank test was used to compare within group changes in the health outcomes. A two-sample Mann-Whitney test was used to compare changes in health outcomes between the CREON2000® and Placebo groups within the treatment period.

Table 1 summarizes the demographic information of subjects that participated in this study. A total of 19 subjects completed the study. One-half of the subjects were Caucasian and the other half were African American. Sixty-eight percent of the participants were male. Two of the homes evaluated had two children in each home. After clinical and environmental assessments ("BASELINE"), the patients were randomized in 2 groups. In the homes of the patients of the CREON2000® Group, CREON2000® units were installed. Group Placebo received Placebo units.

TABLE 1

| Descriptive Statistics of the Study Population | | | |
|---|---|---|---|
| | Group CREON2000: | Group Placebo: | All |
| Intervention | Invention | Placebo | |
| Population | n = 11 | n = 8 | n = 19 |
| Mean Age (yrs) | 9.6 | 12 | 10.6 |
| (Min-Max) | 5-17 | 7-15 | 5-17 |
| Gender (% male) | 73 | 63 | 68 |
| Race(% AA) | 55 | 50 | 53 |

Clinical Outcomes at the Baseline.

Table 2 summarizes mean and median values of clinical outcomes at the baseline: PEFR variability (PEFRvar), FEV1, asthma and rhinoconjunctivitis (RC) symptom severity scores, RC and asthma quality of life scores in subjects.

TABLE 2

Means(SD) and Medians(Min, Max) of Clinical Outcomes at the Base Line

| Characteristic | Mean (SD) CREON2000 Group | Mean (SD) Placebo Group | Median, (Min, Max) CREON2000 Group | Median, (Min, Max) Placebo Group |
|---|---|---|---|---|
| | | Pulmonary functions | | |
| PEFRvar | 0.096 (0.136) | 0.098 (0.039) | 0.046 (0.009, 0.47) | 0.112 (0.030, 0.137) |
| FEV1, l/s | 1.7 (1.04) | 2.17 (0.44) | 1.4 (0.6, 4.5) | 2.37 (1.5, 2.6) |
| | | Asthma Symptoms Severity Scores: | | |
| Wheezing | 0.77 (0.53) | 0.75 (0.98) | 0.75 (0., 1.61) | 0.38 (0.07, 3.0) |
| Shortness of breath | 0.63 (0.35) | 0.87 (0.88) | 0.68 (0., 1.04) | 0.64 (0.07, 2.71) |
| Chest tightness | 0.46 (0.31) | 1.05 (0.65) | 0.39 (0., 1.0) | 1.04 (0.07, 1.82) |
| Cough | 1.06 (0.42) | 1.29 (0.82) | 0.93 (0.18, 0.71) | 1.06 (0.43, 3.0) |
| | | Days with symptom of asthma within 2 wk before the baseline | | |
| Days of Wheeze | 7 (4.90) | 4.75 (4.28) | 6 (0.0, 14) | 4 (1.0, 14) |
| Days when child had Shortness of breath | 6.09 (4.07) | 6.63 (4.68) | 6 (0.0, 14) | 6.5 (0.5, 14) |
| Days of Chest tightness | 4.64 (3.92) | 8.19 (4.28) | 4.5 (0.0, 14) | 9.5 (1.0, 12.5) |
| Days when child had Cough | 8.95 (3.36) | 9.38 (2.80) | 8.5 (2.0, 13.5) | 9.5 (5.0, 13) |

(CREON2000 Group, n = 11; Placebo Group, n = 8)

Baseline means of groups CREON2000® and Placebo for each outcome were not significantly different ($p>0.05$) based on unpaired t-tests adjusted for≠variances Baseline medians of groups CREON2000® and Placebo for FEV1 only were significantly different ($p<0.05$) based on Mann-Whitney U test.

Efficacy Results

The CREON2000® group showed significant improved PEFRvar, significant reduction of asthma severity, and number of days with asthma symptoms (table 3-4). The difference of these characteristics between CREON2000® group and Placebo group was statistically significant. Other characteristics improved but did not reach statistical significance at 0.05 level.

TABLE 3

Clinical outcomes of the trial

| Characteristic | CREON2000 group | Placebo group | Difference | P-value |
|---|---|---|---|---|
| Pulmonary functions | | | | |
| PEFRvar | | | | |
| Mean (SD) | 0.082 (0.121) | 0.113 (0.062) | −0.031 | |
| Median (Min, Max) | 0.037 (0.010, 0.404) | 0.105 (0.035, 0.200) | −0.068 | 0.03 |
| FEV1, l/s | | | | |
| Mean (SD) | 1.89 (1.12) | 2.29 (0.44) | −0.4 | |
| Median (Min, Max) | 1.5 (0.6, 4.9) | 2.37 (1.6, 3.0) | −0.87 | 0.32 |
| Asthma Symptom Severity Scores: | | | | |
| Wheezing | | | | |
| Mean (SD) | 0.23 (0.36) | 0.40 (0.70) | −0.17 | |
| Median (Min, Max) | 0.0 (0.0, 1.11) | 0.02 (0.0, 1.61) | −0.02 | 0.4 |
| Shortness of breath | | | | |
| Mean (SD) | 0.16 (0.24) | 0.58 (0.66) | −0.42 | |
| Median (Min, Max) | 0 (0.0, 0.64) | 0.22 (0.0, 1.48) | −0.22 | 0.04 |
| Chest tightness | | | | |
| Mean (SD) | 0.1 (0.17) | 0.55 (0.64) | −0.45 | |
| Median (Min, Max) | 0 (0.0, 0.50) | 0.3 (0.0, 1.63) | −0.3 | 0.04 |
| Cough | | | | |
| Mean (SD) | 0.47 (0.50) | 0.93 (1.09) | −0.46 | |
| Median (Min, Max) | 0.43 (0.0, 1.64) | 0.71 (0.0, 3.18) | −0.28 | 0.26 |

Results of measurements of pulmonary functions and asthma symptom scores after the intervention are presented in Table 3. Data are expressed as Mean (Standard Deviation) and Median (Min, Max). The improvements in PEFRvar and symptom scores are indicated by negative values of these variables. Patients in the CREON2000® treatment group showed statistically significant improvements in their pulmonary functions and asthma symptom scores and fewer days with the symptoms of asthma when compared to placebo.

The CREON2000® group reported significantly fewer numbers of days with asthma symptoms than Placebo group (Table 4)

TABLE 4

Days with the symptoms of asthma after the intervention. Days with symptom of asthma within 2 weeks

| Characteristic | CREON2000 group | Placebo group | Difference | P-value |
|---|---|---|---|---|
| Days of Wheeze | | | | |
| Mean (SD) | 2.86 (4.55) | 3.69 (6.23) | −0.83 | |
| Median (Min, Max) | 0 (0.0, 14.0) | 0.25 (0.0, 14.0) | −0.25 | 0.24 |
| Days when child had Shortness of breath | | | | |
| Mean (SD) | 1.59 (2.50) | 5.19(5.48) | −3.60 | |
| Median (Min, Max) | 0 (0.0, 7.5) | 2.75 (0.0, 12.0) | −2.75 | 0.02 |
| Days of Chest tightness | | | | |
| Mean (SD) | 1.05 (1.65) | 4.88 (5.32) | −3.83 | |
| Median (Min, Max) | 0 (0.0, 5.0) | 3.5 (0.0, 13.0) | −3.50 | 0.04 |

TABLE 4-continued

Days with the symptoms of asthma after the intervention. Days with symptom of asthma within 2 weeks

| Characteristic | CREON2000 group | Placebo group | Difference | P-value |
|---|---|---|---|---|
| Days when child had Cough | | | | |
| mean (SD) | 5.23 (5.04) | 5.81 (5.34) | −0.06 | |
| Median (Min, Max) | 5 (0.0, 14.0) | 7 (0.0, 14.0) | −2.00 | 0.28 |

Improvements in pulmonary function were associated with CREON2000® treatment. (Table 3). Clinically and statistically significant improvements in PEFRvar, asthma symptom severity scores and in the number of days with the symptom were observed in CREON2000® treatment group compared to placebo. Improvements in FEV1, were also observed in the CREON2000® group, being statistically significant compared to the baseline.

The trial demonstrated that the treatment was more effective than placebo at improving clinical outcomes such as PEFR variability, severity of asthma and number of days of shortness of breath and chest tightness. Improvement in other clinical outcomes did not reach level of statistical significance.

Peak expiratory flow rate variability is a dynamic measurement that best reflects changes in asthma control over time as a result of environmental or therapeutic influences. In CREON2000® group PEFRvar was significantly improved. The between-group difference for PEFRvar of 30.7 percentage points was statistically significant.

In addition the statistically significant reductions of the severity of the chest tightness by 75% and the shortness of breath by 78% along with reductions in wheezing (57%) and cough (56%) was found in the CREON2000® group.

The improvements were also seen in reduction of the number of days when the child had shortness of breath and chest tightness. In the CREON2000® group the number of days with shortness of breath was lower by 4.4 day per 2-week period and the number of days with the chest tightness by 4.4 day per 2-week period. These improvements were clinically and statistically significant (P<0.04).

Safety Results

There were no deaths reported during the study. There were non serious adverse events due the intervention in the study. The study demonstrated that the CREON2000® ultraviolet irradiation system was safe and effective at improving PEFR variability, reducing the severity of asthma and number of days with asthma symptoms.

CONCLUSION

This study in asthmatic children aged six to seventeen years demonstrated that the children in the treatment group significantly improved pulmonary functions, reduced asthma severity and the number of days with asthma symptoms compared to placebo group.

In summary, providing to the patient, during 6-24 hours per day, the air for breathing specifically treated by ultraviolet radiation, with the wavelength 180-400 nm and with the amount of incident UV radiation which applies to said treated air at 2-100 J/m.sup.3 hr, is an effective and well-tolerated treatment with no side effects for children with allergic asthma.

EXAMPLE 2

Treating and Preventing Asthma by providing treated air for breathing and reduced dosage of medicine.

After one month of the treatment according to the invention 11 asthmatic patients in the treatment group in the study described in Example 1 demonstrated an improvement in pulmonary functions and a reduction in the severity and in the number of days with asthma symptoms. 8 of the 11 patients in the treatment group kept their medication diaries before and after the treatment. Seven patients, who kept the diaries had a history consistent with moderate persistent asthma, one patient had history consistent with severe persistent asthma. After one month of the treatment according to the invention, all 7 patients with moderate persistent asthma in addition to the improvement of their health demonstrated a reduction of the dosage of controller medicine and of the risque (reliever) medicine.

The comparison of the results before and after treatment, according to the invention, confirmed, that for all seven patients with moderate persistent asthma the average daily dosage of controller medicine was reduced by 2.5 times and the average daily dosage of risqué (reliever) medicine was reduced by 5.3 times.

The treatment of asthmatic patients, by the provision of treated air for breathing, according to the invention, allowed the patients to achieve an improvement of health along with significant reduction of usage of asthma medications.

While the present invention has been described with particular reference to the treatment of human patients for asthma, it is possible that the invention may also be applicable to the treatment of other pulmonary diseases or conditions such as rhinitis.

The system and method of the present invention may also be engaged in the treatment of breathing disorders in other mammals. An example is reactive airway disease in horses. Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a patient having a disease of allergic airways, selected from the group consisting of asthma, rhinitis and sinusitis, using treated air for breathing, the method comprising of steps of:

providing an enclosed facility with constantly circulating treated air for breathing containing particles;

administering the treated air for breathing containing particles to the patient for more than six hours daily over a two week period; and wherein treated air for breathing containing particles is specifically irradiated to a therapeutic level by an effective amount of incident ultraviolet radiation from a UV lamp, wherein the effective amount of incident UV radiation which is applied to said treated air for breathing containing particles is 2-100 J/m$^3$ hr, so that administration to the patient of the treated air for breathing containing particles for more than six hours daily enables after the two week period a reduction of the severity of the disease and the dose of medication for the treatment of the disease of airways.

2. The method of claim 1 wherein the treated air for breathing containing particles is irradiated by parallel array of beams.

3. The method of claim 1 where ultraviolet radiation being comprised of radiation with the wave length of 180-400 nm.

4. The method of claim 1 wherein the effective amount of incident UV radiation which is applied to said treated air for breathing containing particles is 16-55 J/m$^3$ hr.

5. A method according to claim 1 comprising the steps of:

providing a patient with a baseline medication usage history;

subjecting the patient to treated air for breathing containing particles; and achieving a reduction from the baseline medication usage.

6. The method according to claim 1 wherein the patient is taking one or more the following medications: inhaled corticosteroids; cromolyn; nedocromil; anti-leukotrienes; theophylline; inhaled long-acting beta$_2$ agonist; inhaled short-acting beta$_2$ agonist; anticholinergic; oral steroids.

7. A method of treating a patient diagnosed with asthma and having a baseline medication usage of controller medicine and risqué (reliever) medicine, using treated air for breathing containing particles, the method comprising of steps of:

providing an enclosed facility with constantly circulating treated air for breathing containing particles, wherein treated air for breathing containing particles is specifically irradiated to a therapeutic level by an effective amount of incident ultraviolet radiation from a UV lamp, wherein the effective amount of incident UV radiation which is applied to said treated air for breathing containing particles is 2-100 J/m$^3$ hr;

administering the treated air to the patient daily from 6 to 24 hours in the enclosed facility over a two week period so that after the period of two weeks of the treatment, a reduction in medication usage occurs from the baseline medication usage for one or both of the average daily dosage of controller medicine or the average daily dosage of risqué (reliever) medicine.

8. The method of claim 7 wherein the patient has at least a moderate persistent asthma condition.

9. The method of claim 7 wherein the reduction from the baseline medication usage of the controller is a reduction of about 2.5 times from the baseline usage.

10. The method of claim 7 wherein the reduction of risqué (reliever) medicine is a reduction of about 5 times from the baseline usage.

11. The method of claim 5 wherein the patient has at least a moderate persistent asthma condition.

12. The method of claim 11 wherein the reduction of baseline medication usage of the controller is a reduction of about 2.5 times from the baseline usage.

13. The method of claim 11 wherein the reduction of risqué (reliever) medicine is a reduction of about 5 times from the baseline usage.

14. The method according to claim 1 wherein the disease is rhinitis.

15. The method according to claim 1 wherein the disease is sinusitis.

16. The method according to claim 1 wherein treated air for breathing containing particles circulates through the facility at a rate of 1-15 air changes per hour.

17. The method of claim 7 wherein the effective amount of incident UV radiation which is applied to said treated air for breathing containing particles is 16-55 $J/m^3$ hr.

* * * * *